United States Patent

Oikawa et al.

[11] Patent Number: 6,060,290
[45] Date of Patent: May 9, 2000

[54] ESTERASE AND METHODS FOR THE PRODUCTION OF OPTICALLY ACTIVE CHROMAN COMPOUNDS

[75] Inventors: Toshihiro Oikawa; Nobuhiro Fukuhara; Yasuko Matsuba, all of Fukuoka, Japan

[73] Assignee: Mitsui Chemicals Incorporated, Japan

[21] Appl. No.: 09/118,275

[22] Filed: Jul. 17, 1998

[30] Foreign Application Priority Data

Jul. 18, 1997 [JP] Japan ................................ 9-193949
Aug. 1, 1997 [JP] Japan ................................ 9-219758
Nov. 20, 1997 [JP] Japan ................................ 9-319995

[51] Int. Cl.⁷ .............................. C12P 17/06; C12N 9/18
[52] U.S. Cl. ........................ 435/125; 435/197; 435/280
[58] Field of Search .................... 435/280, 125, 435/197

[56] References Cited

U.S. PATENT DOCUMENTS 5,658,796 8/1997 Rossi, Jr. et al. ........................ 435/280

*Primary Examiner*—Herbert J. Lilling
*Attorney, Agent, or Firm*—Burns, Doane, Swecker & Mathis, L.L.P.

[57] ABSTRACT

Optically active chroman-3-acetic acids and optically active chroman-3-acetic acid esters can be obtained by treating a mixture of (3R)- and (3S)-chroman-3-acetic esters of formula (I)

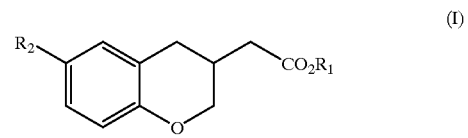

[wherein $R_1$ is a straight or branched alkyl group having 1–5 carbon atoms and $R_2$ is a hydrogen atom or substituted or unsubstituted amino group]

is treated with an esterase which has an optically selective hydrolyzing activity or microorganisms which carry said hydrolase, or a preparation therefrom. A novel esterase derived from bacteria of genus Pseudonocardia can also be used as said esterase.

13 Claims, No Drawings

ESTERASE AND METHODS FOR THE PRODUCTION OF OPTICALLY ACTIVE CHROMAN COMPOUNDS

BACKGROUND OF THE INVENTION

1. Field of the Invention

The present invention relates to a novel esterase which is useful as a catalyst for the hydrolyses of esters, methods for the isolation of said esterase, methods for the kinetic resolution of a mixture of a (R)-form and a (S)-form of an ester compound using said esterase, and methods using said esterase for producing optically active chroman-3-acetic acids and esters thereof, which are useful as medicinal materials.

Furthermore, the present invention relates to methods for producing optically active chroman-3-acetic acids and esters thereof, wherein a mixture of (3R)- and (3S)-chroman-3-acetic acid esters represented by the general formula (I) described below is treated with an ester hydrolase which has an optically selective hydrolyzing activity or microorganisms which carry said hydrolase, or a preparation therefrom.

2. Description of the Related Art

A number of attempts have been made in recent years to apply enzymes in organic syntheses. In particular, the use of esterases, which have high substrate specificities for the optically selective hydrolysis of various ester compounds selectively to thereby obtain optically active compounds, or for producing chiral compounds from prochiral ester compounds, has high industrial efficacy.

An esterase derived from porcine liver is generally used in such purposes as mentioned above but its high cost and limited availability precludes its industrial usage. The use of esterases from microbial sources in place of the esterase derived from porcine liver has been tried. Since enzymes derived from different organisms are characteristically different in their substrate specificities, the selectivity and reaction rate of the enzymes markedly vary depending on the compounds to which the enzymes are applied.

A 6-aminochroman-3-acetic acid ester disclosed in European Patent Publications, EP 0709370 and EP 0760364, is a useful intermediate of an antiplatelet. However, no esterase which shows high optical selectivity for 6-aminochroman-3-acetic acid esters and which can effectively hydrolyze them has been reported.

An objective of the present invention is to find an esterase which is optically selective and useful as a catalyst for producing optically active chroman-3-acetic acids and esters thereof, which are useful as medicinal materials.

Another objective of the present invention is to provide methods for the simple and efficient production of optically active chroman-3-acetic acids and esters thereof.

SUMMARY OF THE INVENTION

As a result of intensive studies to search for a method for the simple and efficient production of optically active chroman-3-acetic acids and esters thereof, the present inventors found that optically active chroman-3-acetic acids and esters thereof can be obtained by treating a mixture of (3R)- and (3S)-chroman-3-acetic acid esters with an ester hydrolase which has an optically selective hydrolyzing activity or microorganisms which carry said hydrolase, or an enzyme preparation therefrom. Furthermore, the present inventors found a novel esterase, which has an optically selective hydrolyzing activity and shows excellent heat and pH stability, from a microorganism of genus Pseudonocardia using a variety of purification techniques and thus came to complete the present invention.

Namely, the present invention relates to a novel esterase found in a microorganism of genus Pseudonocardia which is useful as a catalyst for hydrolyses of esters, methods for the isolation of said esterase, methods for the kinetic resolution of a mixture of (R) and (S) ester compounds using said esterase, and methods using said esterase for producing optically active chroman-3-acetic acids and esters thereof, which are useful as medicinal materials.

Furthermore, the present invention relates to methods for producing optically active chroman-3-acetic acids and esters thereof, wherein a mixture of (3R)- and (3S)-chroman-3-acetic acid esters represented by the formula (I):

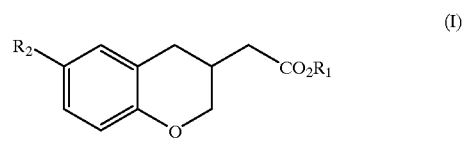

(I)

[wherein $R_1$ is a straight or branched alkyl group having 1–5 carbon atoms and $R_2$ is a hydrogen atom or substituted or unsubstituted amino group]
is treated with an ester hydrolase which has an optically selective hydrolyzing activity or microorganisms which carry said hydrolase, or a preparation therefrom.

DETAILED DESCRIPTION OF THE INVENTION AND PREFERRED EMBODIMENTS

The present invention will be explained in greater detail as follows:

(1) Enzyme-Carrying Microorganisms and Method for Culturing the Same

The target novel esterase is contained in cells of *Pseudonocardia thermophila* FERM-BP-6275 (deposited under Acceptance Number for Deposit FERM-BP-6275 on Mar. 2, 1998 at the National Institute of Bioscience and Human-Technology Agency of Industrial Science and Technology, 1–3, Higashi 1-chome, Tsukuba-shi, Ibaraki-ken, 305-8566, Japan). These cells can be cultured according to any known method. Any medium known as a nutrient medium for general microorganisms can be used. Organic nutrient sources such as meat extract, yeast extract, malt extract, peptone and NZ amine; carbon sources such as glucose, maltose, sucrose, starch and organic acids; nitrogen sources such as ammonium sulfate, urea and ammonium chloride; inorganic nutrient sources such as phosphates, magnesium, potassium and iron; and vitamins can be used in appropriate combinations. The cells are cultured aerobically in a medium at a pH between 6 and 9 at a temperature between 30° C. and 60° C., preferably between 45° C. and 55° C. Culturing is carried out for 1–7 days until the target esterase content reaches its maximum.

(2) Purification of the Enzyme

The enzyme can be purified using a conventional enzyme purification method. Cells are harvested from the completed culture by centrifugation, and mechanically decomposed using an sonication, FRENCH® PRESSURE CELL PRESS, DYNO®-MILL or the like. Solids such as cell debris are removed by centrifugation to obtain a crude enzyme solution. The enzyme is then purified by salting out with ammonium sulfate or other salts, gel filtration, ion exchange chromatography, hydrophobic chromatography, crystallization or the like. An example will be described in Example 1.

(3) Measurement of Enzyme Activity

A reaction mixture (1 ml) containing 10 μmol of racemic 6-aminochroman-3-acetic acid methyl ester, 0.1 mmol potassium phosphate buffer (pH 7.2) and an appropriate amount of esterase was reacted at 55° C. for 30 minutes. After the reaction, a portion of the reaction mixture was diluted with a 10 mM sodium phosphate buffer solution (pH 6.0)—30% acetonitrile solution, and 6-aminochroman-3-acetic acid methyl ester and 6-aminochroman-3-acetic acid were each quantitatively measured by high performance liquid chromatography. Elution was carried out on an inertsil ODS-2 column (a product of GL Science) using a 0mM sodium phosphate buffer solution (pH 6.0)—30% acetonitrile as the carrier at a flow rate of 0.7 ml/minute. Absorbance at 254 nm was measured for detection. Next, an equivalent volume of chloroform was added to the remaining reaction solution to extract the remaining 6-aminochroman-3-acetic acid methyl ester. The chloroform was then removed by distillation under vacuum and the resulting residue was dissolved in ethanol and further diluted with a hexane/ethanol solution (3/2,v/v). (3S)-6-aminochroman-3-acetic acid methyl ester and (3R)-6-aminochroman-3-acetic acid methyl ester in the solution thus prepared were each quantitatively measured to determine optical purity. Elution was carried out on a CHIRALCEL OD-H optical resolution column (a product of DAICEL CHEMICAL INDUSTRIES, LTD) using a hexane/ethanol solution (3:2 in the volume ratio) as a carrier at a flow rate of 0.5 ml/minute. Absorbance at 254 nm was measured for detection.

The amount of enzyme which hydrolyzes 1 μmol of 6-aminochroman-3-acetic acid ethyl ester per minute was defined as one unit.

(4) Homogeneity of the Enzyme

SDS polyacrylamide gel electrophoresis was carried out by the Laemmli method on a 10–20% gel using a tris-glycine buffer solution (Nature 227, 680, 1970). After staining with Coomassie brilliant blue, a homogeneous protein band was observed. The molecular weight of this protein was estimated to be 50000±2000 from a comparison with known standard proteins.

(5) Properties of the Enzyme

The esterase of the present invention showed the following properties:

(1) Enzyme Action

The enzyme acts as a catalyst in the hydrolysis of an ester compound into a compound having a carboxyl group and an alcohol compound, and in an ester exchange reaction between an ester compound and an alcohol compound.

(2) Substrate Specificity

The enzyme predominantly hydrolyzes (R) forms of 6-aminochroman-3-acetic acid esters.

For esters of straight-chain fatty acids and p-nitrophenol, the lesser the number of carbon atoms in the fatty acid, the stronger is the hydrolytic activity.

(3) Molecular Weight

The molecular weight of the enzyme is 50000±2000 (SDS-PAGE).

(4) Optimal pH

Hydrolysis optimally takes place at pH 7–10.

(5) Optimal Temperature

Hydrolysis optimally takes place between 55° C. and 60° C. in a 0.1M phosphate buffer solution (pH 7.2).

(6) Temperature Stability

90% of the hydrolyzing activity can be maintained for 30 minutes at pH 7.2 and at temperatures below 60° C.

(7) pH Stability

The enzyme is stable at a pH range of 5–10.

(8) Inhibitors

Upon treatment with various inhibitors in a 0.1 M phosphate buffer solution (pH 7.2) at 30° C. for 30 minutes, the enzyme loses its activity by 30% with copper sulfate (1 mM), by 85% with phenylmethylsulfonyl fluoride (0.1 mM) and by 15% with diisopropyl fluorophosphate (0.5 mM). No reduction in the enzyme activity is observed with sodium lauryl sulfate (5 mM) or sodium deoxycholate (5 mM). More details will be described in the Examples hereinafter.

As mentioned above, the enzyme of the present invention is an esterase which acts stereospecifically on 6-aminochroman-3-acetic acid esters and has excellent heat-resistance and pH stability.

The compounds of the formula (I) can be stereoselectively hydrolyzed in the presence of the above esterase from *Pseudonocardia thermophila* FERM-BP-6275.

The present invention also include optical resolution using ester hydrolase provided by microorganisms. Microorganisms which contain the esterase or the ester hydrolase used in the present invention can be any microorganisms which predominantly hydrolyze either one of the optical compounds in a mixture of (3R)- and (3S)-chroman-3-acetic acid esters. Examples of such microorganisms include those of genus Pseudonocardia, genus Flavobacterium and genus Thermoactinomyces. Particular examples of such microorganisms include *Pseudonocardia thermophila* FERM-BP-6275, *Flavobacterium okeanokoites* FERM-BP-6276, *Thermoactinomyces sacchari* ATCC-27375, *Flavobacterium okeanokoitos* IFO 15880. The strains FERM BP-6275 and FERM BP-6276 were deposited in the National Institute of Bioscience and Human-Technology of The Agency of Industrial Science and Technology in the Ministry of International Trade and Industry, 1–3, Higashi 1 Chome, Tsukuba-shi, Ibaraki-ken, 305-8566, Japan under these deposition numbers on Feb. 27, 1998 under the Budapest Treaty. The strain having the ATCC number is kept and available for the public from the ATCC (The American Type Culture Collection, 12301 Parklawn Drive, Rockville, Md. 20852, U.S.A.). The strain having the IFO number is also publicly available from the Institution for Fermentation Osaka, 17–85, Juso-honmachi, 2-chome, Yodogawa-ku, Osaka, 532 Japan.

These microorganisms are not particularly restricted provided they have the abilities necessary for the present invention. Examples of microorganisms to be used include mutant strains obtained, for example, by ultraviolet radiation or by the use of a mutating agent, or those obtained by induction by genetic engineering.

Microbial cultures or preparations therefrom are not particularly restricted provided they have the necessary abilities necessary for the present invention. Examples of microbial cultures include culture fluids and microbial cells. Examples of preparations from cultures include washed cells, dried cells, culture supernatants, decomposed cells such as cell debris, cell autodigests, cell extracts or enzyme preparations purified or partially purified using a conventional method. Furthermore, these microbial cultures and preparations therefrom can be immobilized for use; immobilizing methods include treatment with the polyacrylamide, alginic acid and carrageenan, or immobilization onto an appropriate carrier using known methods such as the covalent bond method and absorption method.

Any medium generally used in this field to culture microorganisms can be used. For example, organic nutrient sources such as meat extract, yeast extract, malt extract, peptone and NZ amine; carbon sources such as glucose, maltose, sucrose, starch and organic acids; nitrogen sources such as ammonium sulfate, urea and ammonium chloride; inorganic nutrient sources such as phosphates, magnesium, potassium and iron and vitamins can be used in appropriate combinations. Culturing can be carried out aerobically at a pH between 6 and 9 at a temperature between 20° C. and 60° C. However, culturing at a temperature between 28° C. and 37° C. is preferable for *Flavobacterium okeanokoitos* FERM BP-6276. Culturing at a temperature between 45° C. and 55° C. is preferable for *Pseudonocardia thermophila* FERM-BP-6275 and *Thermoactinomyces sacchari* ATCC-27375. Culturing is carried out for 1–7 days until the target esterase content reaches its maximum.

The living culture cells and culture supernatant are prepared by a procedure such as centrifugation and filtration from the fluid obtained by culturing the microorganisms as mentioned above. Washed cells are prepared by washing living cells with a physiological saline solution. Dried cells are prepared by lyophilizing or acetone-drying living cells or washed cells. Decomposed cells are prepared using various physicochemical procedures such as ultrasound decomposition, french press, osmotic pressure, freeze-fusion, use of lytic enzymes or treatment with surfactants and organic solvents. A purified or partially purified enzyme was obtained, for example, from decomposed cells or the culture supernatant by fractionation using a conventional method such as ammonium sulfate precipitation, ion exchange chromatography, gel filtration, or hydrophobic chromatography.

Examples of $R_1$ group in the formula (I) include straight and branched alkyl groups having 1 to 5 carbon atoms, more specifically methyl, ethyl, propyl, isopropyl or butyl group, more preferably a methyl group or ethyl group.

Examples of the substitution group when $R_2$ is an amino group include acetyl, tert-butoxycarbonyl or benzyloxycarbonyl group.

A reaction medium, which have no adverse effect on the reaction, or mixtures thereof, may be used for the opticalselective hydrolysis. The reaction medium may be a homogeneous system using water or a mixture of water and a water-miscible solvent, or a two-phase system using a mixture of water and a non-water-miscible solvent.

Examples of the water-miscible solvent include straight and branched alkyl alcohol having 1 to 4 carbon atoms, acetonitrile, N,N-dimethylformamide, dimethylsulfoxide and tetrahydrofuran. The water-miscible solvent may be used in an amount can range between 0.1 and 20.0% (v/v) in water.

Examples of the non-water-miscible solvent include organic solvents such as toluene and xylene. The amount of the non-water-miscible organic solvent may range between 1.0–40.0% (v/v) in water.

The concentration of racemic chroman-3-acetic acid esters to be added to the reaction solvent is generally 0.01–50% (w/v), preferably 0.01–20% (w/v).

The reaction is carried out at room temperature or with heating, preferably at a temperature between 15° C. and 70° C., more preferably between 20° C. and 60° C.

The pH of the reaction solution varies depending on the type of the hydrolyzing enzyme or source microorganisms. However, the reaction is generally carried out at a pH between 3 and 11. In the case where the pH of the reaction solution changes as hydrolysis proceeds, it is preferable to control the pH at the optimum pH.

Also, reactivity between the substrate and enzyme can be enhanced by adding a surfactant or the like to the reaction solution.

Isolation of optically active chroman-3-acetic acid esters and optically active chroman-3-acetic acids after optically selective hydrolysis can be very easily carried out by the extraction of optically active chroman-3-acetic acid esters with a non-water-miscible extraction solvent in the homogenous system using water or a mixture of water and water-miscible solvent, or by the separation of the organic solvent layer and the water layer in the two-phase system using a mixture of water and a non-water-miscible solvent or water and a mixture of a water-miscible solvent and a non-water-miscible solvent. Depending on the intended usage, the resulting optically active chroman-3-acetic acid esters in the organic solvent layer can be used as is in solution, or as synthesis intermediates after removing the solvent. Optically active chroman-3-acetic acid of higher optical purity can be obtained by crystallization using an appropriate solvent. Optically active chroman-3-acetic acids in the water layer can be obtained by a known method such as concentrated crystallization after removing cellular components using a known method such as filtration.

EXAMPLE

The present invention will be explained in greater detail by the following examples. However, it should be understood that these examples are not intended as a definition of the limits of the invention.

Example 1

Method of Culturing Esterase-Containing Microorganisms

To a sterilized medium (1 L) containing 0.1% yeast extract, 0.1% meat extract (Ehrlich), 0.2% NZ amine (Type 1) 0.5% sodium chloride, 0.05% potassium dihydrogenphospate, 0.1% dipotassium hydrogenphosphate, 0.01% magnesium sulfate, and 1.0% soluble starch (pH 7.4) was inoculated 5% culture of *Pseudonocardia thermophila* FERM BP-6275 which had been preliminary cultured in the same medium. After culturing anaerobically at 52° C. for 96 hours, the resulting culture was centrifuged to obtain 10 g of wet cells.

Example 2

Purification of Esterase

The cells obtained in Example 1 were suspended in 100 ml of a 0.05 M potassium phosphate buffer solution (pH 7.2) (hereinafter referred to as buffer), dispersed by ultrasound treatment and then decomposed using a french press. Cell debris were removed by centrifugation (15000× g, 20 minutes) to obtain a cell-free extract. Ammonium sulfate was added up to 60% to the cell-free extract and an active fraction was obtained as a precipitate by centrifugation. This precipitate was dissolved in 100 ml of the buffer and the solution was subjected to gel filtration using Ultrogel® ACA44 (a product of Pharmacia) as a carrier. An active fraction was collected and applied on a DEAE TOYOPEARL 650M (a product of TOSOH) column and eluted with the buffer containing 0.8 M ammonium sulfate and the buffer using a linear concentration gradient. The resulting active fraction was concentrated using ultrafiltration and dialyzed against the buffer. Thus, the esterase was homogeneously purified. The purification process is summarized in Table 1.

TABLE 1

| Process | Total activity (Total unit) | Total protein (mg) | Specific activity (Unit/mg) |
|---|---|---|---|
| 1. Cell-free liquid extract | 677 | 185 | 3.7 |
| 2. Ammonium sulfate precipitation (<60%) | 425 | 125 | 3.4 |
| 3. Gel filtration (Ultrogel ® ACA44 fraction range MW: 10,000–100,000) | 358 | 25 | 14.6 |
| 4. DEAE TOYOPEARL 650S | 262 | 10 | 26.2 |
| 5. Phenyl TOYOPEARL 650M | 143 | 2 | 71.5 |

Example 3
Optically Selective Hydrolysis of Racemic 6-aminochroman-3-acetic Acid Esters Racemic 6-aminochroman-3-acetic acid methyl ester or racemic 6-aminochroman-3-acetic acid methyl ester was hydrolyzed under the following conditions using the esterase homogeneously purified in Example 2.

A reaction solution (1 ml) containing 0.1 mmol potassium phosphate buffer (pH 7.2), 10 μmol racemic 6-aminochroman-3-acetic acid methyl ester and an appropriate amount of esterase was reacted at 55° C. for 30 minutes. After the reaction, a portion of the reaction solution was diluted with a 10 mM sodium phosphate buffer solution (pH 6.0)—30% acetonitrile solution, and 6-aminochroman-3-acetic acid methyl ester and 6-aminochroman-3-acetic acid was each quantitatively measured by high performance liquid chromatography. Elution was carried out on an inertsil ODS-2 column (a product of GL Science) using a 10 mM sodium phosphate buffer solution (pH 6.0)—30% acetonitrile solution as the carrier at a flow rate of 0.7 ml/minute. Absorbance at 254 nm was measured for detection. Next, an equivalent volume of chloroform was added to the remaining reaction solution to extract the remaining 6-aminochroman-3-acetic acid methyl ester. The chloroform was then removed by distillation under vacuum and the resulting residue was dissolved in ethanol and further diluted with a hexane/ethanol (3/2,v/v) solution. (3S)-6-aminochroman-3-acetic acid methyl ester and (3R)-6-aminochroman-3-acetic acid methyl ester in the solution thus prepared were each quantitatively measured to determine optical purity. Elution was carried out on a Chiral Cell OD-II optical resolution column (a product of Daicel) using hexane/ethanol (3:2 in the volume ratio) as a carrier at a flow rate of 0.5 ml/minute. Absorbance at 254 nm was measured for detection.

The above procedure was repeated using 6-aminochroman-3-acetic acid ethyl ester in stead of 6-aminochroman-3-acetic acid methyl ester, and then the amount of (R) 6-aminochroman-3-acetic acid in the reaction solution and the amounts of (S)6-aminochroman-3-acetic acid ethyl ester and (R) 6-aminochroman-3-acetic acid ethyl ester in the hexane/ethanol solution were determined in the same manner as described above.

Results are shown in Table 2.

TABLE 2

Optically selective hydrolysis of racemic 6-aminochroman-3-acetic acid esters

| Racemic substrate | 6-Aminochroman-3-acetic acid (μ mol) | 6-Aminochroman-3-acetic acid ester (μmol) | Optical purity (% ee) |
|---|---|---|---|
| 6-Aminochroman-3-acetic acid methyl ester | 6.0 | 4.0 | S 99 |
| 6-Aminochroman-3-acetic acid ethyl ester | 6.2 | 3.8 | S 99 |

Example 4
Hydrolysis Using Esters of Straight-Chain Fatty Acids and as Substrates An appropriate amount of the enzyme solution was added to 2.5 ml of a 0.2 M potassium phosphate buffer solution (pH 7.0) containing 1 mM of one of various p-nitrophenyl esters. The resulting reaction solution was incubated at 45° C. for 8 minutes. The reaction was stopped by adding 1 ml of methanol and then an increase in absorbance at 400 nm was determined. In control samples, the buffer solution was used in place of the enzyme solution. Relative activities for p-nitrophenyl esters were calculated from changes in the absorbance. Results are shown in Table 3.

TABLE 3

Relative activities for p-nitrophenyl esters (based on 100% activity for p-nitrophenyl acetic acid ester)

| Substrate | Relative activity (%) |
|---|---|
| p-Nitrophenyl acetic acid ester | 100 |
| p-Nitrophenyl capric acid ester | 12 |
| p-Nitrophenyl lauric acid ester | 0.6 |

Example 5
Optimum pH for the Enzyme Reaction

Optimum pH was studied using the esterase homogeneously purified in Example 2. A reaction mixture (1.0 ml) containing 10 μmol of racemic 6-aminochroman-3-acetic acid methyl ester, 0.1 mmol of one of the buffers providing various pH ranges as described below and 0.1 unit of esterase were incubated at 55° C. for 30 minutes. After the reaction, an equivalent volume of chloroform was added to extract the remaining 6-aminochroman-3-acetic acid methyl ester. The chloroform was then removed by distillation under vacuum and the resulting residue was dissolved in ethanol and further diluted with a hexane/ethanol solution (3/2,v/v). (3S)-6-aminochroman-3-acetic acid methyl ester and (3R)-6 -aminochroman-3-acetic acid methyl ester were each quantitatively measured by high performance liquid chromatography. Enzyme activity was measured by a decrease in the amount of 6-aminochroman-3-acetic acid methyl ester.

The buffers used were potassium phosphate buffers for pH 5.0–7.2, tris-HCl buffers for pH 8.0–9.5 and CAPS buffer (Good buffer) for pH 10.0. As shown in results in Table 4, the optimum pH was at a range of 8.0–10.0.

Example 6 pH Stability of the Enzyme pH stability was studied using the esterase homogeneously purified in Example 2. 0.5 units of the esterase was added to a 0.1 M buffer solution at a specified pH as in Example 5 and the solution was maintained at 30° C. for 30 minutes, after which the remaining activity was measured using 0.1 unit of the enzyme. The relative activity was based on 100% esterase activity of a control sample without pH treatment. Results in Table 4 show that there was little change in the activity at a pH range of 5.0–10.0.

TABLE 4

Optimum pH and pH stability

| pH | Optimum pH#<br>(Example 5) | pH stability*<br>(Example 6) |
| --- | --- | --- |
| 5.0 | 28 | 97 |
| 6.0 | 65 | 98 |
| 6.5 | 80 | 100 |
| 7.2 | 90 | 100 |
| 8.0 | 93 | 100 |
| 8.5 | 93 | 100 |
| 9.5 | 94 | 100 |
| 10.0 | 100 | 99 |

: Relative activity based on 100% activity obtained at pH 10.
*: Relative activity based on 100% activity obtained at pH 7.2 without enzyme reaction after retained for 30 minutes at the specified pH.

Example 7

Optimum Temperature for the Enzyme Reaction

The reaction was carried out in the same manner as described in Example 5 except that the reaction temperatures were 30, 40, 50, 55, 60 and 70° C. and the buffer used were potassium phosphate buffer (pH 7.2). Results showed that the activity was highest at 60° C. The relative activity is based on 100% activity obtained at 60° C. (Table 5).

Example 8

Temperature Stability of the Enzyme

Temperature stability was studied using the esterase homogeneously purified in Example 2. 0.1 units of the esterase was added to a 0.1 mmol potassium phosphate buffer solution (pH 7.2) to make a total volume of 0.95 ml. The admixture was maintained at a specified temperature, i.e., 30, 40, 50, 55, 60 or 70° C. for 30 minutes. To this, 0.05 ml of 0.2 M racemic 6-aminochroman-3-acetic acid methyl ester hydrochloride was added and the reaction was carried out at 55° C. for 30 minutes, after which the remaining activity was measured. The relative activity was based on 100% esterase activity obtained without heat treatment. Results in Table 5 show that more than 90% of the activity was maintained at temperatures up to 60° C.

TABLE 5

Optimum temperature and temperature stability

| Temperature<br>(° C.) | Optimum<br>temperature#<br>(Example 7) | Temperature<br>stability*<br>(Example 8) |
| --- | --- | --- |
| 30 | 24 | 100 |
| 40 | 43 | 100 |
| 50 | 69 | 100 |
| 55 | 75 | 100 |
| 60 | 100 | 90 |
| 70 | 35 | 0 |

: Relative activity based on 100% activity obtained at 60° C.
*: Relative activity based on 100% activity obtained at 55° C. without enzyme reaction after retaining for 30 minutes at the specified temperature.

Example 9

Effect of Inhibitors

Effect of various inhibitors on the esterase homogeneously purified in Example 2 was studied. 0.1 unit of the esterase, a 0.1 mmol potassium phosphate buffer solution (pH 7.2) and a specified inhibitor were mixed to make a total volume of 0.95 ml and the admixture was maintained at 30° C. for 30 minutes. To this, 0.05 ml of 0.2 M racemic 6-aminochroman-3-acetic acid methyl ester hydrochloride was added and the reaction was carried out at 55° C. for 30 minutes, after which the remaining activity was measured. The relative activity was based on 100% esterase activity obtained without inhibitors. Results are shown in Table 6. Of metals, $Cu^{2+}$ was inhibitory. Of others, phenylmethylsulfonyl fluoride (PMSF), a protease inhibitor, and diiospropylfluorophosphoric acid (DFP) were inhibitory. No marked reduction in the enzyme activity was observed with surfactants such as sodium lauryl sulfate (5 mM) or sodium deoxycholate (5 mM) (Table 6).

TABLE 6

Effect of inhibitors

| Inhibitor | Relative activity |
| --- | --- |
| None | 100 |
| $FeSO_4$ 1 mM | 92 |
| $CoCl_2$ 1 mM | 102 |
| $MnSO_4$ 1 mM | 99 |
| $NiCl_2$ 1 mN | 92 |
| $CuSO_4$ 1 mM | 21 |
| $CaCl_2$ 1 mM | 96 |
| $ZnCl_2$ 1 mM | 101 |
| EDTA 5 mM | 103 |
| PMSF 0.1 mM | 84 |
| DFP 0.5 mM | 6 |
| DTT 0.1 mM | 102 |
| SDS 5 mM | 99 |
| Sodium deoxycholate | 102 |

Example 10

Optically Selective Hydrolysis of Racemic 6-aminochroman-3-acetic Acid Methyl Ester by Microorganisms Various microorganisms were cultured each on an agar slant medium under the conditions shown in Table 7. One platinum loopful of the cell culture was suspended in 1 ml of a reaction solution containing 2.5 mg of racemic 6-aminochroman-3-acetic acid methyl ester hydrochloride and 0.1 mmol of potassium phosphate (pH 7.2). The reaction solution was reacted at 30° C. for 16 hours, after which unreacted 6-aminochroman-3-acetic acid methyl ester was extracted with an equivalent volume of chloroform. The chloroform was then removed by distillation under vacuum and the resulting residue was dissolved in ethanol and further diluted with a hexane/ethanol solution (3/2,v/v). (3S)-6-aminochroman-3-acetic acid methyl ester and (3R)-6-aminochroman-3-acetic acid methyl ester were each quantitatively measured. Elution was carried out on a Chiral Cell OD-II optical resolution column (a product of Daicel) using hexane/ethanol (3:2 in the volume ratio) as a carrier at a flow rate of 0.5 ml/minute. Absorbance at 254 nm was measured for detection. Results are shown in Table 7.

TABLE 7

Selective hydrolysis of racemic 6-aminochroman-3-acetic acid methyl ester by microorganisms

| Microbial strain | Culture conditions | S-ester content (mg/ml) | R-ester content (mg/ml) |
|---|---|---|---|
| Flavobacterium okeanokoitos IFO 15880 | A | 0.98 | 0.00 |
| Thermoactinomyces sacchari | B | 1.20 | 0.73 |

Culture condition A:

| Yeast extract | 0.5% |
|---|---|
| Bactotryptone | 1.0% |
| Sodium chloride | 1.0% |
| Agar | 1.5% |
| pH: 7.3; culture temperature: | 30° C. |

Culture condition B:

| Yeast extract | 0.1% |
|---|---|
| Meat extract | 0.1% |
| NZ amine | 0.2% |
| Maltose | 1.0% |
| Agar | 1.5% |
| pH: 7.3; culture temperature: | 45° C. |

Example 11
Optically Selective Hydrolysis of Racemic 6-aminochroman-3-acetic Acid Methyl Ester by *Pseudonocardia thermophila*

To 10 ml of a sterilized medium (pH 7.4) containing 0.1% yeast extract, 0.1% meat extract (Ehrlich), 0.2% NZ amine (TYPE 1), 0.5% sodium chloride, 0.05% potassium dihydrogenphosphate, 0.1% dipotassium hydrogenphosphate, 0.01% magnesium sulfate, and 1.0% soluble starch was inoculated 5% culture of *Pseudonocardia thermophila* FERM BP-6275which had been preliminary cultured in the same medium. The culture was carried out at 52° C. for 72 hours. Wet cells obtained by centrifugation were added to 50 ml of a reaction solution (pH 8.0, adjusted with potassium hydroxide) containing 1 g of racemic 6-aminochroman-3-acetic acid methyl ester. Hydrolytic reaction was carried out at 55° C. for 3 hours while maintaining the pH at 8.0 with a 2% potassium hydroxide solution. After the reaction, 20 ml of toluene were added and unreacted a 6-aminochroman-3-acetic acid methyl ester was extracted. Most of the remaining 6-aminochroman-3-acetic acid methyl ester was extracted into the toluene layer and hydrolyzed 6-aminochroman-3-acetic acid was present in the water layer. (S) 6-aminochroman-3-acetic acid methyl ester with a purity of more than 99% was obtained by concentrating the toluene layer (yield: 40%).

Example 12
Optically Selective Hydrolysis of Racemic 6-aminochroman-3-acetic Acid Ethyl Ester by *Pseudonocardia thermophila*

To 10 ml of a sterilized medium (pH 7.4) containing 0.1% yeast extract, 0.1% meat extract (Ehrlich), 0.2% NZ amine (TYPE 1), 0.5% sodium chloride, 0.05% potassium dihydrogenphosphate, 0.1% dipotassium hydrogenphosphate, 0.01% magnesium sulfate, and 1.0% soluble starch was inoculated 5% culture of *Pseudonocardia thermophila* FERM BP-6275 which had been preliminary cultured in the same buffer. The culture was carried out at 52° C. for 72 hours. Wet cells obtained by centrifugation were added to 50 ml of a reaction solution (pH 8.0, adjusted with potassium hydroxide) containing 1 g of racemic 6-aminochroman-3-acetic acid ethyl ester hydrochloride. Hydrolytic reaction was carried out at 55° C. for 6 hours while maintaining the pH at 8.0 with a 2% potassium hydroxide solution. After the reaction, 20 ml of toluene were added and unreacted 6-aminochroman-3-acetic acid ethyl ester was extracted. Most of the remaining 6-aminochroman-3-acetic acid ethyl ester was extracted into the toluene layer and hydrolyzed 6-aminochroman-3-acetic acid was retained in the water layer. (S) 6-aminochroman-3-acetic acid ethyl ester with a purity of more than 99% was obtained by concentrating the toluene layer (yield: 35%).

EFFECTIVENESS OF THE INVENTION

The present inventors have found a novel esterase, having excellent heat and pH stability, which can catalyze the hydrolysis of esters with an extremely small amount under the normal pressure and at a normal temperature and has an optically selective hydrolyzing activity on useful medicinal intermediates, chroman-3-acetic acids and esters thereof. This esterase can be used for the simple and efficient production of optically active chroman-3-acetic acids and esters thereof, which are useful as medicinal intermediates. Furthermore, optically active chroman-3-acetic acids and optically active chroman-3-acetic acid esters can easily and effectively be produced from a mixture of (3R)- and (3S)-chroman- 3-acetic acid esters by treating with the esterase which has an optically selective hydrolyzing activity or microorganisms which carry said hydrolase, or a preparation therefrom.

What is claimed is:
1. An isolated and purified esterase which has the following physicochemical properties:
 (1) Enzyme action:
  the enzyme acts as a catalyst in the predominant hydrolysis of (R) forms of 6-aminochroman-3-acetic acid esters into (R) forms of 6-aminochroman-3-acetic acid and alcohol, and in an ester exchange reaction between an ester compound and alcohol;
 (2) Substrate specificity:
  for esters of straight-chain fatty acids and p-nitrophenol, the lesser the number of carbon atoms in the fatty acids, the stronger is the hydrolytic activity;
 (3) Molecular weight:
  the molecular weight of the enzyme is 50000±2000 (SDS-PAGE);
 (4) Optimal pH:
  hydrolysis optimally take place at pH 7–10;
 (5) Optimal temperature:
  hydrolysis optimally takes place at 55° C. to 60° C.;
 (6) Temperature stability:
  90% of the hydrolyzing activity can be maintained for 30 minutes at pH 7.2 and at temperatures below 60° C.;

(7) pH stability:
  the enzyme is stable at a pH range of 5–10;
(8) Inhibitors:
  upon treatment with various inhibitors in a 0.1 M phosphate buffer solution (pH 7.2) at 30° C. for 30 minutes, the enzyme loses its activity by 30% with copper sulfate (1 mM), by 85% with phenylmethylsulfonyl fluoride (0.1 mM) and by 15% with diisopropyl flourophosphate (0.5 mM) and no reduction in the enzyme activity is observed with sodium lauryl sulfate (5 mM) or sodium deoxycholate (5 mM).

2. A method for producing the esterase of claim 1, wherein microorganisms of genus Pseudonocardia which produce the esterase of claim 1 are cultured and the esterase is isolated from the resulting culture.

3. A method as claimed in claim 2, wherein said microorganisms of genus Pseudonocardia is *Pseudonocardia thermophila* FERM-BP-6275.

4. A method for optical resolution of a mixture of a (R)-ester compound and a (S)-ester compound, comprising the steps of
  (a) contacting the esterase described in claim 1 with a mixture of a (R) -ester compound and a (S)-ester compound in a reaction medium to obtain an optically active acid compound by stereoselectively hydrolyzing one of the (R)-ester compound and the (S)-ester compound;
  (b) recovering the optically active acid compound or the optically active ester, which is not hydrolyzed and remains, from the reaction medium.

5. A method as claimed in claim 4, wherein the esterase is one of the forms selected form the group consisting of a isolated and purified enzyme, a crude enzyme preparation, cells of a microorganism having the esterase, a culture supernatant of said microorganism, cell debris of said microorganism and an extract from cells of said microorganism and immobilized the esterase or cells of a microorganism having the esterase.

6. A method as claimed in claim 5, wherein ester compounds are chroman compounds of formula (I):

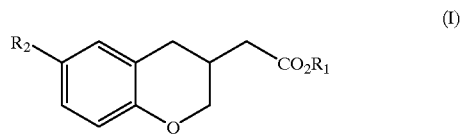

(I)

wherein $R_1$ is a straight or branched alkyl group having 1–5 carbon atoms and $R_2$ is a hydrogen atom or a substituted or unsubstituted amino group.

7. A method as claimed in claims 4, wherein the reaction medium comprises a two-phase system of water and a non-miscible organic solvent.

8. A method as claimed in claim 4, wherein ester compounds are chroman compounds of formula (I):

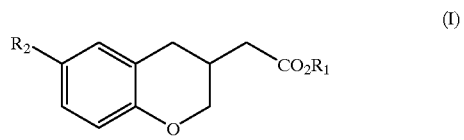

(I)

wherein $R_1$ is a straight or branched alkyl group having 1–5 carbon atoms and $R_2$ is a hydrogen atom or a substituted or unsubstituted amino group.

9. A method as claimed in claim 7, wherein said non-miscible organic solvent is an aromatic carbohydrate.

10. A method as claimed in claim 7, wherein said non-miscible organic solvent is toluene or xylene.

11. A method as claimed in claim 7, wherein the amount of the non-miscible organic solvent to be added is 1.0–40.0% (v/v) in water.

12. A method of claim 6, wherein $R_2$ is an amino group.

13. A method claimed in claim 6, wherein $R_1$ is a methyl group or ethyl group.

* * * * *